(12) United States Patent
Miyazawa et al.

(10) Patent No.: US 10,295,533 B2
(45) Date of Patent: *May 21, 2019

(54) TEST KIT

(71) Applicant: Denka Seiken Co., Ltd., Chuo-ku (JP)

(72) Inventors: Takashi Miyazawa, Gosen (JP); Yuki Shinohara, Gosen (JP)

(73) Assignee: Denka Seiken Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/775,209

(22) PCT Filed: Mar. 12, 2014

(86) PCT No.: PCT/JP2014/056520
§ 371 (c)(1),
(2) Date: Sep. 11, 2015

(87) PCT Pub. No.: WO2014/142181
PCT Pub. Date: Sep. 18, 2014

(65) Prior Publication Data
US 2016/0033501 A1 Feb. 4, 2016

(30) Foreign Application Priority Data
Mar. 13, 2013 (JP) ................. 2013-050976

(51) Int. Cl.
G01N 33/558 (2006.01)
(52) U.S. Cl.
CPC .................. G01N 33/558 (2013.01)
(58) Field of Classification Search
None
See application file for complete search history.

(56) References Cited

U.S. PATENT DOCUMENTS

| 5,356,782 A | 10/1994 | Moorman et al. | |
| 9,897,601 B2 | 2/2018 | Miyazawa et al. | |
| 2002/0098512 A1* | 7/2002 | Goodell | G01N 33/558 435/7.1 |
| 2002/0164670 A1 | 11/2002 | Forrest | |
| 2002/0192839 A1* | 12/2002 | Mink | B01L 3/5023 436/514 |
| 2004/0019301 A1 | 1/2004 | Wong et al. | |
| 2007/0004006 A1* | 1/2007 | Jung | C12Q 1/701 435/69.1 |
| 2008/0210644 A1* | 9/2008 | Milunic | B01D 39/2017 210/767 |
| 2009/0093968 A1* | 4/2009 | Kawamata | G01N 21/78 702/19 |
| 2009/0253219 A1 | 10/2009 | Bauer et al. | |
| 2010/0159599 A1* | 6/2010 | Song | A61F 13/42 436/39 |
| 2011/0076781 A1 | 3/2011 | Liu et al. | |
| 2016/0041161 A1 | 2/2016 | Miyazawa et al. | |

FOREIGN PATENT DOCUMENTS

| JP | H04-318462 | 11/1992 | |
| JP | H08-501387 | 2/1996 | |
| JP | 2001-021562 | 1/2001 | |
| JP | 2002-202307 | 7/2002 | |
| JP | 2003-083970 | 3/2003 | |
| JP | 2003-513244 | 4/2003 | |
| JP | 2007-086026 | 4/2007 | |
| JP | 2008-164520 | 7/2008 | |
| JP | 2010-156571 | 7/2010 | |
| JP | 2011-191317 | 9/2011 | |
| JP | 2012-063175 | 3/2012 | |
| JP | 2012-189346 | 10/2012 | |
| JP | 2012-524279 | 10/2012 | |
| WO | WO-2003/085402 | 10/2003 | |
| WO | WO-2008016268 | 2/2008 | |
| WO | WO-2009123592 | 10/2009 | |
| WO | WO-2011057025 | 5/2011 | |
| WO | WO 2012012500 A1 * | 1/2012 | ............... B01L 9/52 |
| WO | WO-2014/142179 | 9/2014 | |
| WO | WO-2014/142181 | 9/2014 | |

OTHER PUBLICATIONS

"International Application No. PCT/JP2014/056518, International Search Report dated Jun. 10, 2014", (Jun. 10, 2014), 5 pgs.
"International Application No. PCT/JP2014/056520, International Search Report dated Jun. 17, 2014", (Jun. 17, 2014), 5 pgs.
"U.S. Appl. No. 14/775,176, Non Final Office Action dated Apr. 22, 2016", 8 pgs.
"European Application No. 14764277.1, Extended European Search Report dated Sep. 30, 2016", (Sep. 30, 2016), 9 pgs.
"European Application No. 14764552.7, Extended European Search Report dated Sep. 30, 2016", (Sep. 30, 2016), 7 pgs.
"U.S. Appl. No. 14/775,176 Examiners Interview Summary dated Jul. 6, 2017", 3 pgs.

(Continued)

Primary Examiner — Bao Thuy L Nguyen
Assistant Examiner — Ellen J Marcsisin
(74) Attorney, Agent, or Firm — Schwegman Lundberg & Woessner, P.A.

(57) ABSTRACT

The present invention provides a test kit capable of rapid and highly sensitive detection.
The test kit is provided with a first member, which contains a region in which is held a labeling substance with a label immobilized on a substance that specifically binds with a substance to be detected, and a second member, which has a detection zone where the labeling substance is captured through the substance to be detected, which is connected downstream of the first member in the developing direction, and which allows the labeling substance contained in a liquid sample that flows in from the first member, to develop into the detection zone. The first member has a dropping region located furthermost upstream and containing a portion onto which the liquid sample is dropped, a labeling substance holding region connected to the second member and having a containing portion that contains the labeling substance and a non-containing portion that is located upstream of the containing portion and that does not contain the labeling substance, and a backflow prevention region, which is connected between the dropping region and the non-containing portion of the labeling substance holding region, and in which absorbency is set higher than in the dropping region.

4 Claims, 9 Drawing Sheets

(56) References Cited

OTHER PUBLICATIONS

"U.S. Appl. No. 14/775,176, Advisory Action dated Jul. 28, 2017", 4 pgs.
"U.S. Appl. No. 14/775,176, Final Office Action dated Apr. 18, 2017", 9 pgs.
"U.S. Appl. No. 14/775,176, Response filed Aug. 18, 2017 to Final Office Action dated Apr. 18, 2017", 11 pgs.
"U.S. Appl. No. 14/775,176, Response filed Jul. 12, 2017 to Final Office Action dated Apr. 18, 2017", 10 pgs.
"U.S. Appl. No. 14/775,176, Response filed Dec. 29, 2016 to Non Final Office Action dated Sep. 29, 2016", 10 pgs.
"U.S. Appl. No. 14/775,176, Notice of Allowance dated Oct. 5, 2017", 7 pgs.

* cited by examiner

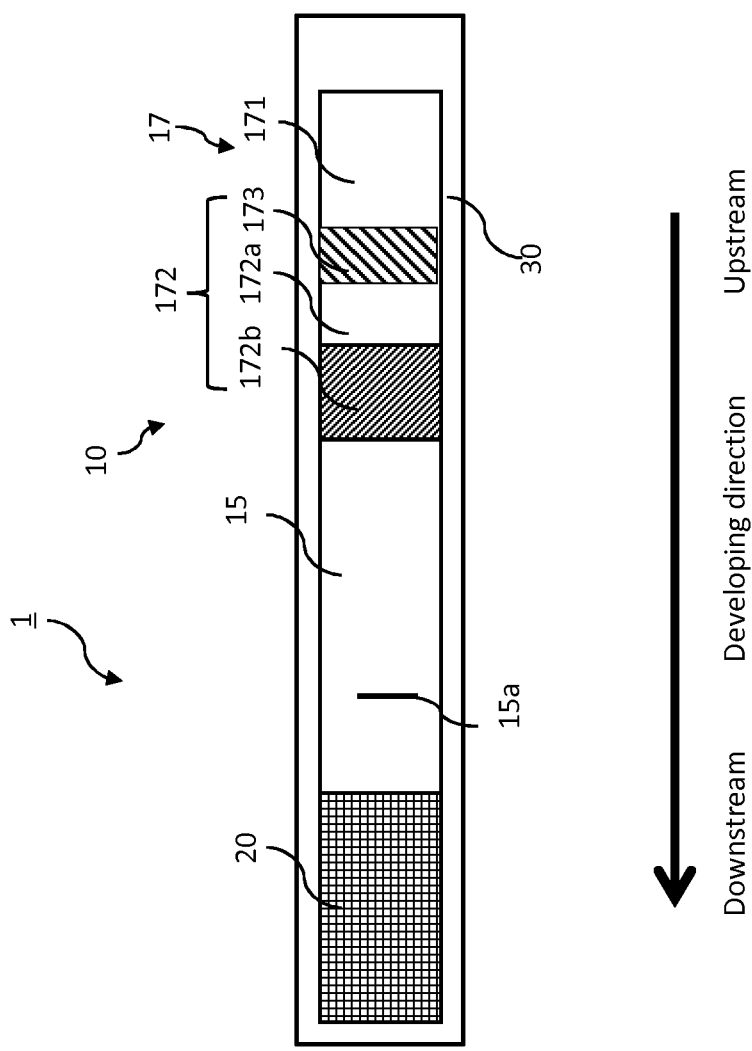

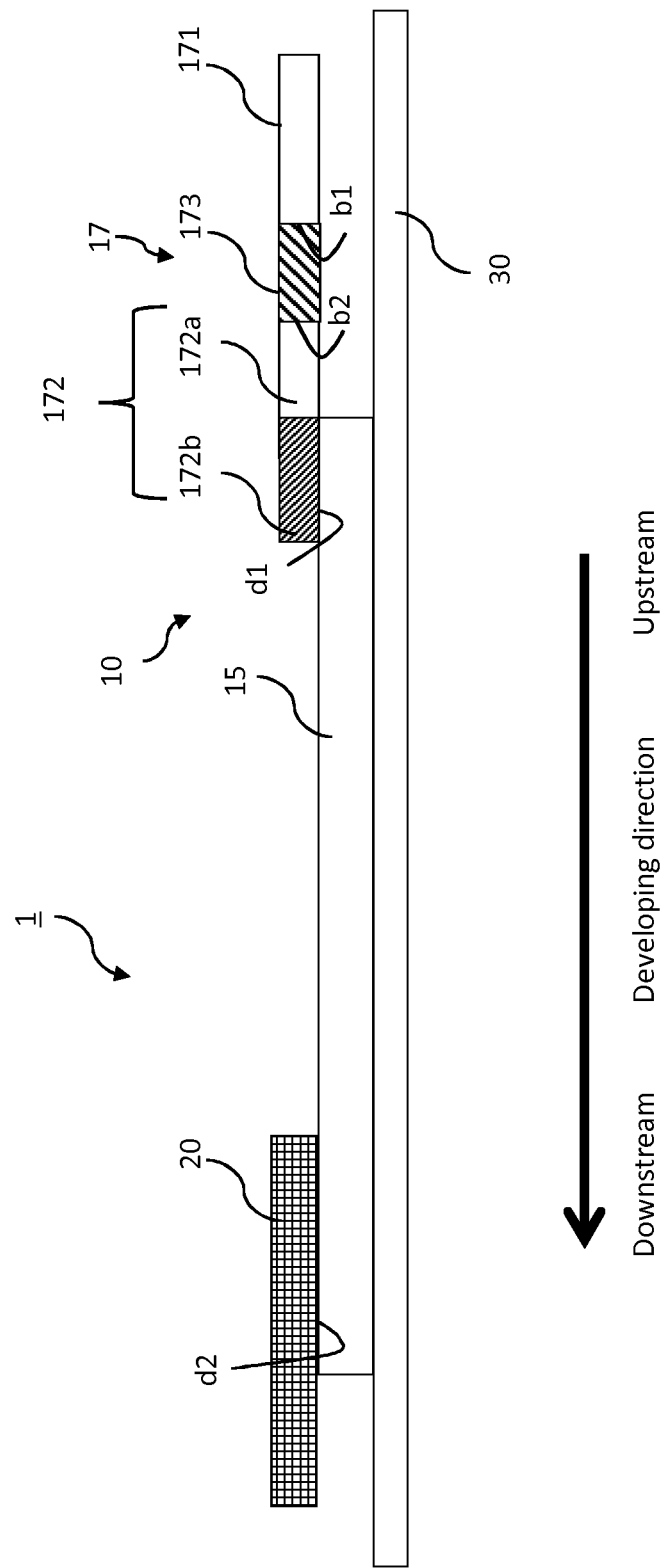

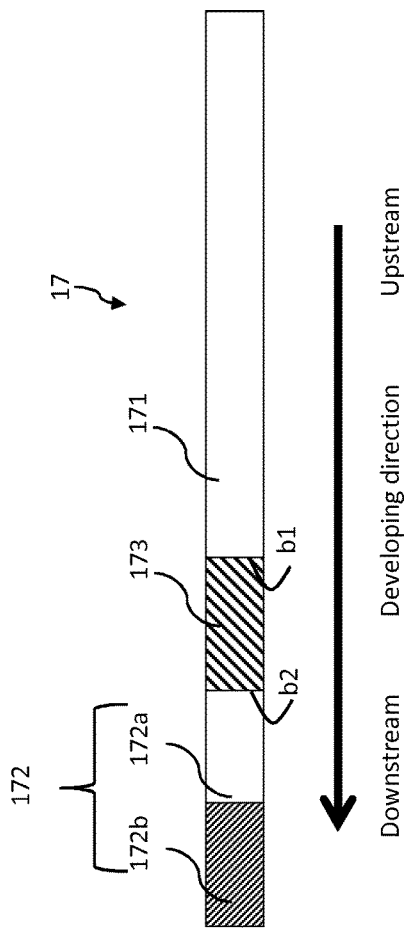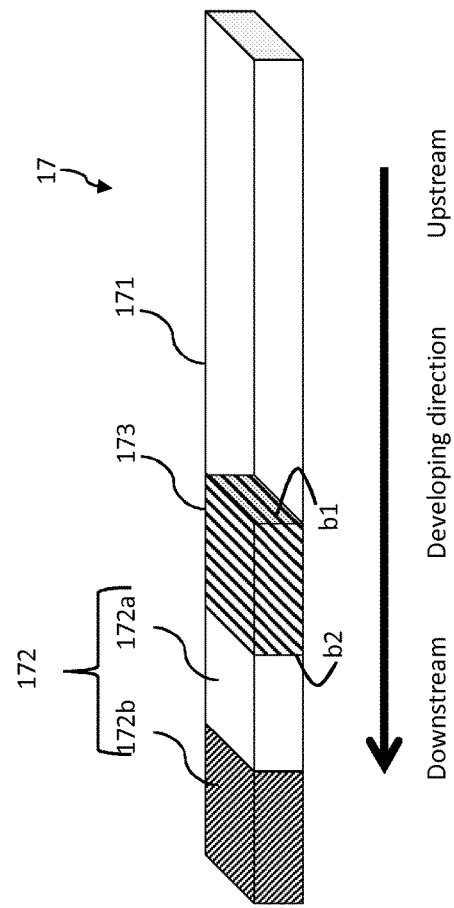

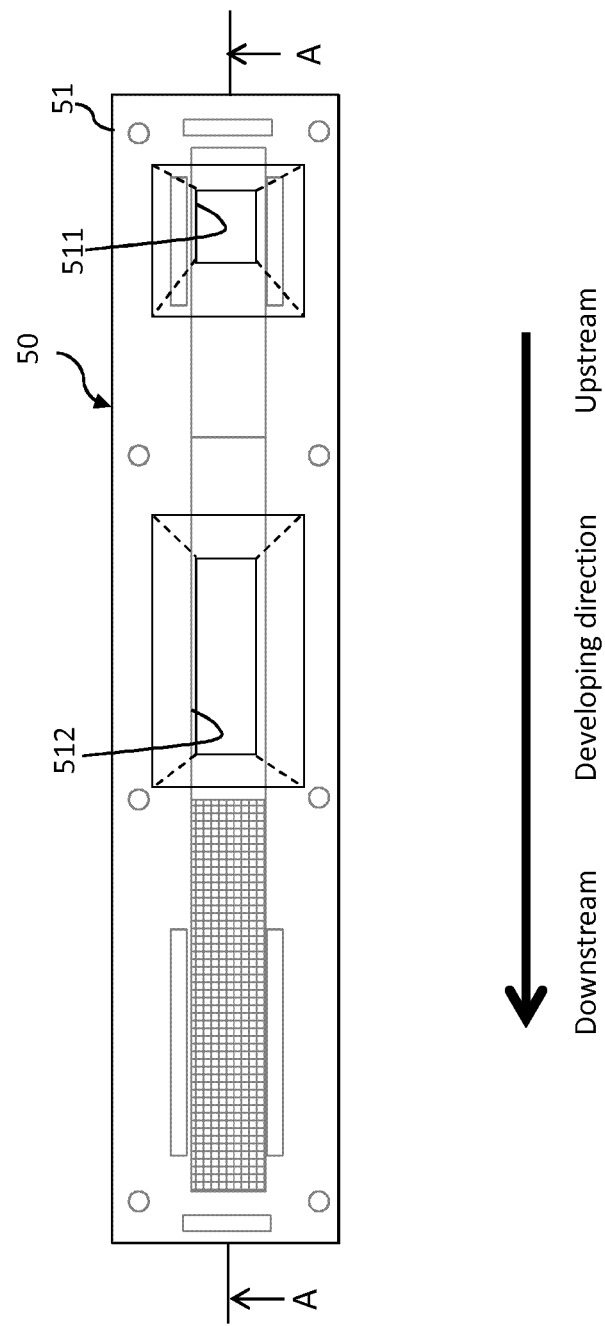
[Fig. 4]

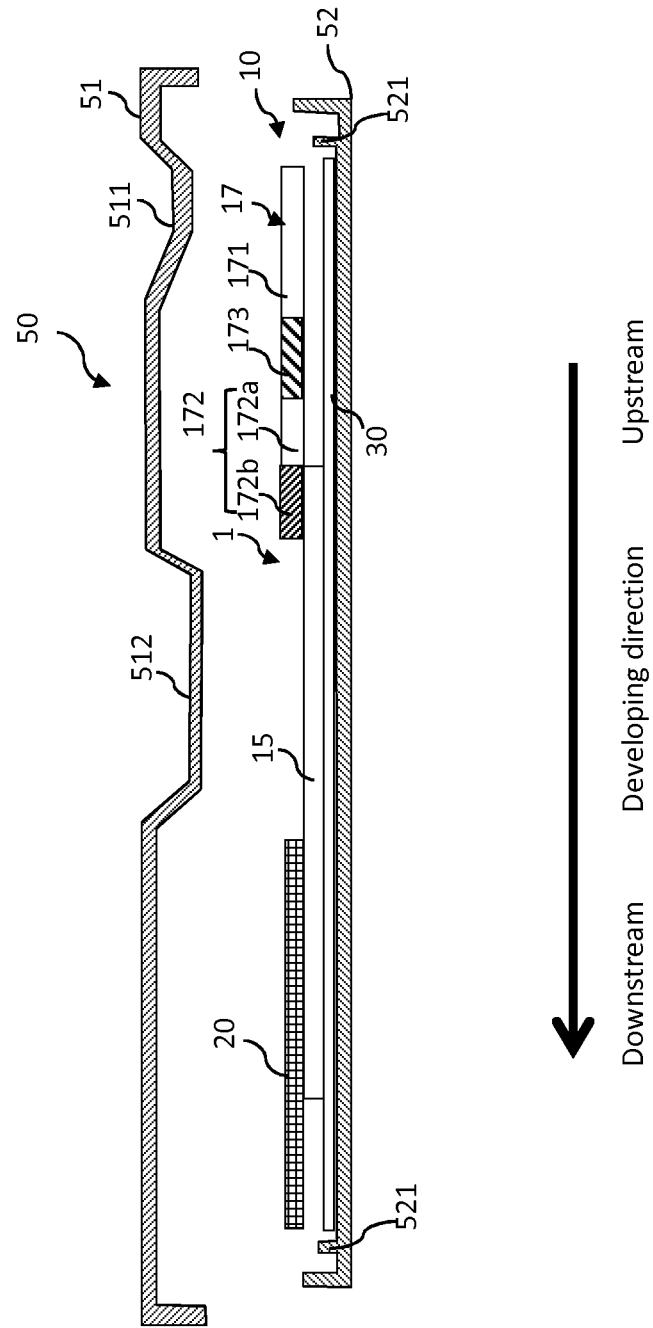

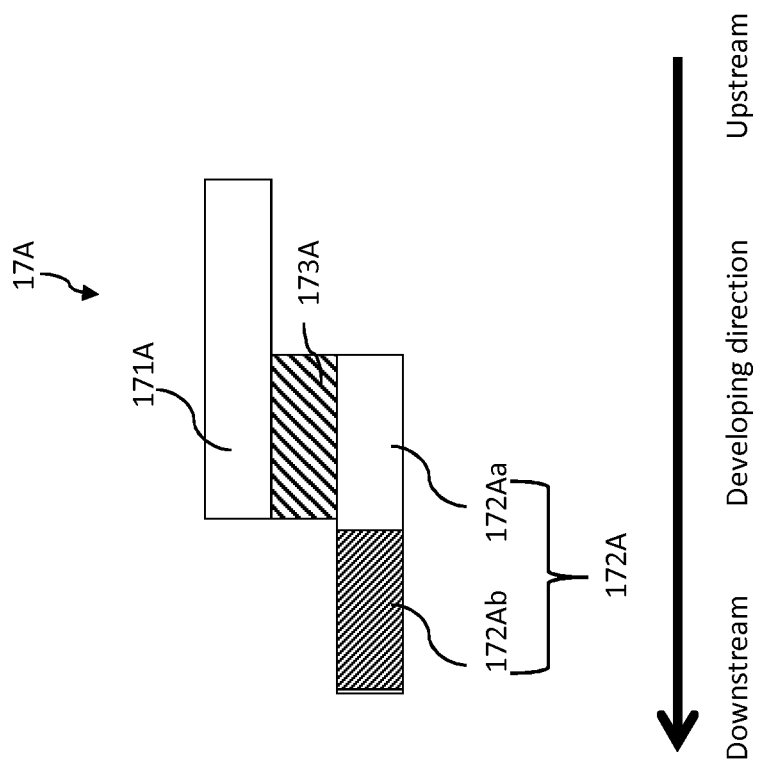

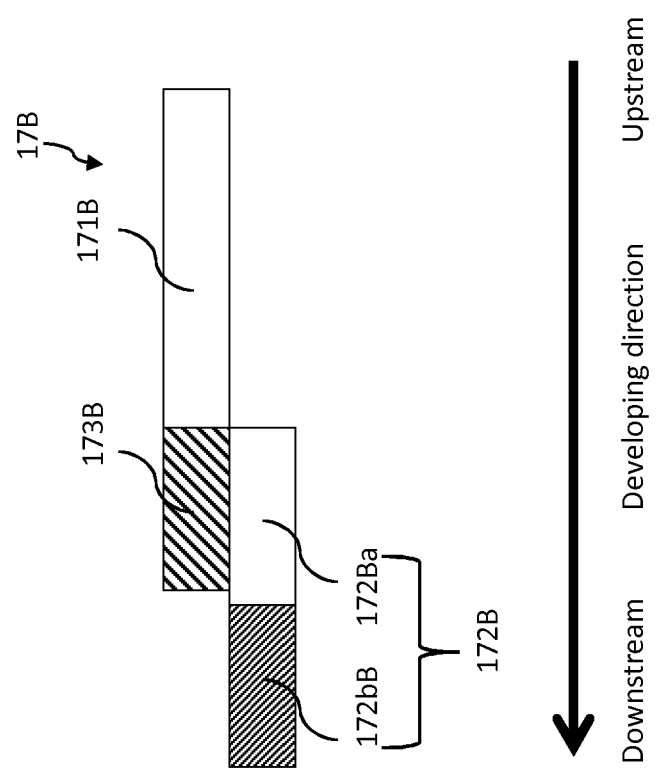
[Fig. 7]

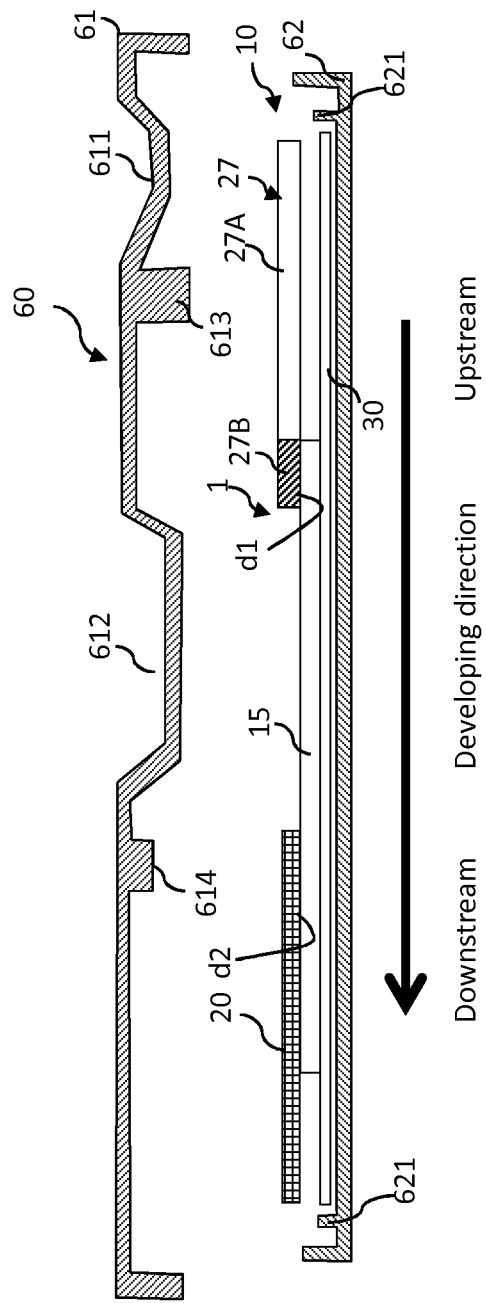

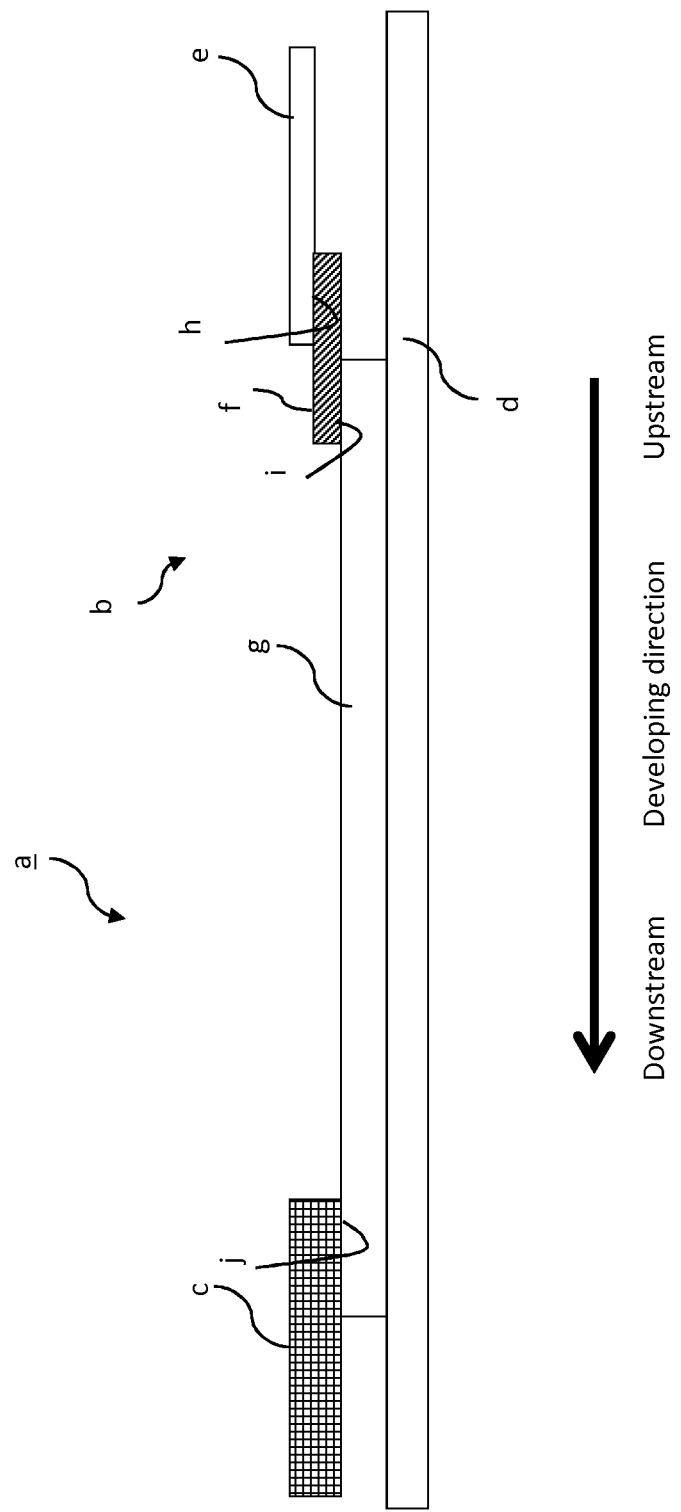
[Fig. 9]

TEST KIT

PRIORITY CLAIM TO RELATED APPLICATIONS

This application is a U.S. national stage application filed under 35 U.S.C. § 371 from International Application Serial No. PCT/JP2014/056520, which was filed 12 Mar. 2014, and published as WO2014/142181 on 18 Sep. 2014, and which claims priority to Japanese Application No. 2013-050976, filed 13 Mar. 2013, which applications and publication are incorporated by reference as if reproduced herein and made a part hereof in their entirety, and the benefit of priority of each of which is claimed herein.

TECHNICAL FIELD

The present invention relates to a test kit that uses immunochromatography.

BACKGROUND ART

Immunochromatography is a known example of an immunoassay method that detects a specific substance to be detected using an antigen-antibody or other specific reaction.

Immunochromatography is a testing method widely used as a Point Of Care Test (POCT). POCT are performed near the patient instead of sending the patient's specimen to a testing facility so as to enable the physician to rapidly assess the test results and promptly initiate treatment. Immunochromatography is used to diagnose infections derived from bacteria and viruses, and particularly infections in cases involving newborns or the elderly having diminished immune strength that require immediate treatment, and is required to demonstrate rapid and highly sensitive detection.

Simple test kits are used for assays based on immunochromatography (see PTL 1). Test kits are kits that consist of (1) allowing a liquid sample to develop downstream by capillary phenomenon, and (2) detecting a substance to be detected in the sample. Whether or not the substance to be detected is contained in the liquid sample is determined by whether or not a test line provided downstream of the liquid in the direction of development is labeled.

FIG. 9 is a side view of a test kit of the prior art that uses immunochromatography. A test kit a has a kit body b, which detects a substance to be detected by developing a liquid sample, an absorbent pad c, which takes up the liquid sample downstream of the kit body b, and a sheet d on which the kit body b and the absorbent pad c are installed. The kit body b has a plurality of members, and more specifically, a liquid dropping pad e, a labeling substance holding pad f and an immobilizing membrane g. At least some of these members e through g are mutually connected to allow development of the liquid sample. The following provides an explanation of each member of the kit body b.

The sample dropping pad e is a pad for dropping the liquid sample.

The labeling substance holding pad f is a pad in which the labeling substance is uniformly held. The labeling substance holding pad f is fabricated by impregnating a pad with a solution containing the labeling substance, followed by drying. Furthermore, the labeling substance referred to here refers to a substance in which a first substance (antibody or antigen), which specifically binds with a substance to be detected (antigen or antibody) in the liquid sample, is immobilized on insoluble carrier particles, an enzyme-labeled ligand or a fluorescence-labeled ligand serving as a label.

The immobilizing membrane g is a pad on which a second substance (antibody or antigen), which specifically binds with a substance to be detected in the liquid sample, is immobilized in the form of a line.

The following indicates typical behavior within the test kit a when using the above-mentioned test kit a.

When a liquid sample is dropped onto the sample dropping pad e, the liquid sample develops through the liquid dropping pad e and flows into the labeling substance holding pad f through an interface h with the labeling substance holding pad f. Then, the labeling substance uniformly held in the labeling substance holding pad f is made to flow out by the liquid sample and flow into the immobilizing membrane g together with the liquid sample through an interface i with the immobilizing membrane g. Moreover, the liquid sample develops through the immobilizing membrane g and is absorbed by the absorbent pad c through an interface j with the absorbent pad c.

As described above, in the case a substance to be detected is contained in the liquid sample, the substance to be detected binds with the first substance of the labeling substance. The second substance immobilized in the form of a line on the immobilizing membrane g becomes an immobilized sample, and the substance to be detected having a labeling substance bound thereto binds therewith and is captured in the form of line. As a result, since the labeling substance is captured in the form of a line, it can be confirmed by viewing the labeled test line and the substance to be detected in the sample is detected.

CITATION LIST

Patent Literature

[PTL 1]
Japanese Patent Application Publication No. 2002-202307

SUMMARY OF INVENTION

Technical Problem

Test kits using immunochromatography are required to demonstrate rapid and highly sensitive detection. Thus, it is necessary that a labeling substance holding pad be allowed to develop to the location of a test line on an immobilizing membrane as rapidly as possible, and that the labeling substance be reliably developed so as not to remain in the vicinity of the test line in order to facilitate identification of the test line.

However, as was previously described, the test kit a of the prior art used the labeling substance holding pad f in which the labeling substance is uniformly held. Consequently, there was the risk of the labeling substance being retained as a result of becoming caught in disturbances in the flow of the liquid sample caused by the liquid sample flowing in from the interface h. In addition, the lower surface of the sample dropping pad e was joined to the upper surface of the labeling substance holding pad f over a comparatively broad range. Consequently, the range in which the liquid flowed from the interface h was broad and the liquid sample flowed into the labeling substance holding pad f with greater intensity than in the case of flowing in using gravity by capillary phenomenon alone, thereby causing an increase in disturbances of the flow of the liquid sample and retention of the labeling substance. In addition, there were also cases in which liquid sample containing the labeling substance retained therein ended up flowing back in opposition to the developing direction. Furthermore, retention here refers to stagnation of the flow of the labeling substance caused by the labeling substance becoming caught in a disturbance in the flow of the liquid sample in the case the upstream to downstream flow of the liquid sample has been disturbed.

Consequently, an excessive amount of time was required for the labeling substance held in the labeling substance holding pad f to reliably develop beyond the location of the test line, thereby inhibiting rapid and reliable development.

Thus, an object of the present invention is to provide a test kit that enables rapid and highly sensitive detection.

Solution to Problem

The test kit is a kit for detecting a substance to be detected contained in a liquid sample by allowing the liquid sample to develop in a developing direction, and is provided with a first member, which contains a region in which is held a labeling substance with a label immobilized on a substance that specifically binds with the substance to be detected, and a second member, which has a detection zone where the labeling substance is captured through the substance to be detected, which is connected downstream of the first member in the developing direction, and which allows the labeling substance contained in the liquid sample that flows in from the first member, to develop into the detection zone. The first member has a dropping region located furthermost upstream and containing a portion onto which the liquid sample is dropped, a labeling substance holding region connected to the second member and having a containing portion that contains the labeling substance and a non-containing portion that is located upstream of the containing portion and that does not contain the labeling substance, and a backflow prevention region, which is connected between the dropping region and the non-containing portion of the labeling substance holding region, and in which absorbency is set higher than in the dropping region.

The first member may be fabricated by processing a single sheet member.

The backflow prevention region is formed by compressing an intermediate region in the lengthwise direction of a sheet member.

The labeling substance holding region is formed by impregnating the sheet member with a solution containing the labeling substance over a region extending from one end of the sheet member in the lengthwise direction thereof to a location that does not reach the backflow prevention region, followed by drying.

The first member may be integrally formed by compressing a member within the labeling substance holding region and/or backflow prevention region.

The test kit is provided with a test kit body having the first member and the second member, and a case that houses the test kit body; and, pressing portions each pressing the intermediate region of the sheet member in the lengthwise direction at each prescribed pressure may be formed in the case.

Advantageous Effects of Invention

According to the present invention, detection can be carried out rapidly and with high sensitivity.

BRIEF DESCRIPTION OF DRAWINGS

FIG. 1 is an overhead view showing one example of a test kit according to a first embodiment.
FIG. 2 is a side view of the test kit of FIG. 1.
FIG. 3A is a side view of a first pad.
FIG. 3B is a perspective view of a first pad.
FIG. 4 is an overhead view showing one example of a case that houses a test kit.
FIG. 5 is a cross-sectional view taken along line A-A of FIG. 4.
FIG. 6 is a side view showing a variation of a first pad.
FIG. 7 is a side view showing another variation of a first pad.
FIG. 8 is a drawing showing a state in which the test kit according to a second embodiment is housed in a case.
FIG. 9 is an overhead view showing a test kit of the prior art.

DESCRIPTION OF EMBODIMENTS

The following provides an explanation of several embodiments of the present invention with reference to the drawings. Furthermore, in the following explanations, duplicate explanations of those portions that have the same structural portions and are indicated with the same reference symbols are omitted as a general rule since they carry out the same operation.

First Embodiment

FIG. 1 is an overhead view showing one example of a test kit 1 according to a first embodiment. FIG. 2 is a side view of the test kit 1 of FIG. 1. FIG. 3A is a side view of a first pad. FIG. 3B is a perspective view of a first pad.

<Configuration of Test Kit>

The test kit 1 is a kit that detects a substance to be detected (antibody or antigen, to apply similarly hereinafter) contained in a liquid sample by allowing the liquid sample to develop in a developing direction (which may be hereinafter simply referred to as the developing direction). More specifically, whether or not a substance to be detected is contained in a liquid sample is determined according to whether or not a test line, which is provided downstream of the liquid sample dropped onto the test kit 1, is labeled. The developing direction of the liquid sample is indicated with an arrow in the drawings.

The test kit 1 has a kit body 10, an absorbent pad 20 and a sheet 30. The sheet 30 is, for example, a widely known waterproof sheet having an adhesive upper surface. The kit body 10 and the absorbent pad 20 are arranged on the upper surface of the sheet 30. The absorbent pad 20 is arranged superimposed on an end portion on the downstream side of the kit body 10, and takes up liquid sample that develops through the kit body 10. The kit body 10 enables determination of the presence or absence of a substance to be detected in the liquid sample by developing the liquid sample.

<Explanation of Each Member>

The kit body 10 has a first member in the form of a multifunctional member 17, and a second member in the form of an immobilizing membrane 15. The multifunctional member 17 contains a region in which is held a labeling substance with a label immobilized on a substance (antibody or antibody, to apply similarly hereinafter) that specifically binds with a substance to be detected. A detailed description of the multifunctional member 17 will be subsequently described.

At least a portion of the immobilizing membrane 15 is connected downstream of the multifunctional member 17 in the developing direction. More specifically, an end portion of the immobilizing membrane 15 on the upstream side thereof in the developing direction is arranged superimposed below an end portion of the multifunctional member 17 on the downstream side thereof in the developing direction. An interface 1*d* is formed by the upper surface of the immobilizing membrane 15 and the lower surface of the multifunctional member 17. In addition, the immobilizing membrane 15 has a higher absorbency and a lower liquid developing speed than any region of the multifunctional member 17. More specifically, the immobilizing membrane 15 is formed with, for example, a fibrous member (film body), such as a nitrocellulose membrane, having finer openings than the multifunctional member 17. Thus, the liquid sample is absorbed through an interface d1 into the immobilizing membrane 15 with greater force (higher absorbency) than during development through the multifunctional member 17.

The immobilizing membrane 15 has a detection zone 15*a* (see FIG. 1) in which a substance (antibody or antigen, to apply similarly hereinafter) that specifically binds with a substance to be detected is immobilized. A test line is labeled as a result of a labeled complex to be subsequently described specifically binding to detection zone 15*a* and the labeling substance being captured in the form of a line. Furthermore, although not shown in the drawing, the immobilizing membrane 15 may also have a control zone that is a region in which a control substance (antibody or antigen, to apply similarly hereinafter) is immobilized. The control zone is preferably arranged on the downstream side of the detection zone 15*a*. In this case, by further holding a control labeling substance, in which insoluble carrier particles and the like for labeling have been immobilized on a substance (antigen or antibody) that specifically binds to the control substance, in the multifunctional member 17, a liquid sample (which contains these labeling substances) can be confirmed to have been developed in the control zone.

The absorbent pad 20 is a pad that absorbs the liquid sample of the kit body 10. At least a portion of the absorbent pad 20 is connected downstream of the immobilizing membrane 15 in the developing direction. More specifically, the end portion on the upstream side of the absorbent pad 20 in the developing direction is placed on the end portion on the downstream side of the immobilizing membrane 15 in the developing direction. As a result, an interface d2 is formed by the upper surface of the absorbent pad 20 and the lower surface of the immobilizing membrane 15. The liquid sample is absorbed by the absorbent pad 20 through the interface d2.

The multifunctional member 17 is formed with a single rectangular sheet-like member (which may also be subsequently referred to as a sheet member). The multifunctional member 17 has a plurality of regions. More specifically, the multifunctional member 17 has a sample dropping region 171, a labeling substance holding region 172 and a backflow prevention region 173. A fibrous member having a uniform opening size, for example, is used for the sheet member, and the multifunctional member 17 is fabricated by processing thereof.

The sample dropping region 171 is located furthermost upstream in the multifunctional member 17 in the developing direction and has a dropping portion onto which the liquid sample is dropped (not shown). The sample dropping region 171 has a prescribed absorbency. More specifically, the sample dropping region 171 is a region in which the fibers thereof have comparatively coarse openings and in which the absorbency thereof is set to be comparatively low and the developing speed thereof is set to be comparatively fast.

The labeling substance holding region 172 is a region that is located furthermost downstream in the multifunctional member 17 in the developing direction and is connected to the immobilizing membrane 15. More specifically, in the example shown in the drawings, only a containing portion 172*b* is arranged at the interface d1 so as to contact the upper surface of the immobilizing membrane 15. The labeling substance holding region 172 has the same absorbency as the sample dropping region 171. More specifically, the labeling substance holding region 172 is a region in which the fibers thereof have comparatively coarse openings and in which the absorbency thereof is set to be comparatively low and the developing speed thereof is set to be comparatively fast.

The labeling substance holding region 172 is a region in which a labeling substance is held. The labeling substance holding region 172 has a containing portion 172*b* that uniformly contains the labeling substance, and a non-containing portion 172*a* that does not contain the labeling substance. The non-containing portion 172*a* is located on the upstream side of the containing portion 172*b* in the developing direction. Here, the labeling substance refers to a substance in which a substance that specifically binds to a substance to be detected (antibody or antigen, to apply similarly hereinafter) in a liquid sample is immobilized on insoluble carrier particles, an enzyme-labeled ligand or a fluorescence-labeled ligand serving as a label. Examples of insoluble carrier particles serving as a label include gold colloids, platinum colloids, colored particles and fluorescent particles.

The labeling substance holding region 172 is formed in the multifunctional member 17 by impregnating the sheet member with a solution containing a labeling substance over a region extending from one end portion of the sheet member in the lengthwise direction thereof (end portion downstream in the developing direction as the multifunctional member 17) to a location that does not reach the backflow prevention region 173, followed by drying. As a result, the containing portion 172*b* and the non-containing portion 172*a* are formed in the labeling substance holding region 172. As a result of forming in this manner, the multifunctional member 17 can be fabricated easily. Furthermore, fabrication of the labeling substance holding region 172 is not limited to the method described above. In addition, the labeling substance of the containing portion 172*b* may also be partially held non-uniformly.

The backflow prevention region 173 is a region that is connected between the sample dropping region 171 and the labeling substance holding region 172. An interface b1 is formed between the sample dropping region 171 and the backflow prevention region 173, and an interface b2 is formed between the backflow prevention region 173 and the labeling substance holding region 172. In addition, the backflow prevention region 173 has a higher absorbency and slower sample developing speed than the adjacent sample dropping region 171 and labeling substance holding region 172. More specifically, the backflow prevention region 173 is, for example, a region in which fiber openings are finer than those of the sample dropping region 171 and the labeling substance holding region 172. Thus, the liquid sample flows into the backflow prevention region 173 through the interface b1 at greater intensity (absorbency) than during development through the liquid dropping region 171, and flows into the labeling substance holding region 172 through the interface b2 at lower intensity (absorbency) than during development through the backflow prevention region 173.

The backflow prevention region 173 is formed by compressing an intermediate region of the sheet member in the lengthwise direction thereof. Thus, the function of preventing backflow can be realized easily by compressing a portion of the sheet member.

In the above-mentioned description, the multifunctional member 17 is formed with a single, rectangular sheet-like member and a difference in absorbency was created between the backflow prevention region 173 and the other regions 171 and 172 by compressing only the backflow prevention region 173. Consequently, the sample dropping region 171 and the labeling substance holding region 172 had the same absorbency. However, the absorbencies (and similarly, developing speeds) of these two regions 171 and 172 are not required to be the same provided the absorbencies thereof are set higher than the absorbency of the backflow prevention region 173. The absorbency of the labeling substance holding region 172 may be set higher than the absorbency of the sample dropping region 171 or may conversely be set lower. In this case, any or all regions of the multifunctional member 17 may be compressed at prescribed compression rates corresponding to the respective required opening size.

In addition, in FIG. 2, only the containing portion 172b is arranged so as to contact the upper surface of the immobilizing membrane 15 at the interface d1. However, the present embodiment is not limited thereto, but rather, for example, not only the containing portion 172b, but also the non-containing portion 172a, may be arranged so as to contact the upper surface of the immobilizing membrane 15. In addition, a portion of the lower surface of the containing portion 172b, for example, may be arranged so as to contact the upper surface of the immobilizing membrane 15. Furthermore, in any case, preferably only the labeling substance holding region 172 contacts the immobilizing membrane 15.

Furthermore, in FIG. 2, although end portions on those sides that do not contact other members in the multifunctional member 17 and the absorbent pad 20 are arranged separated from the sheet 30, these end portions may also be adhered to the sheet 30.

The upper surface of the test kit 1 may also be made to be covered with a cover not shown made of a waterproof material. In this case, the cover may be transparent to enable viewing of the test line, and an opening may be formed in the dropping portion that allows a liquid sample to pass through.

In addition, the test kit 1 may be used by housing in a case. FIG. 4 is an overhead view showing on example of a case 50. FIG. 5 is a cross-sectional view taken along line A-A of FIG. 4.

The case 50 has a case body 52 that houses a test kit 1 and a cover 51 that covers the case body 52. A plurality of projecting portions 521 that position the test kit 1 are provided on the case body 52. An opening 511 for dropping a liquid sample onto the sample dropping region 171 and an opening 512 for viewing the test line on the immobilizing membrane 15 are formed in the cover 51. The test kit 1 may be housed in the case 50 while covered with a cover or the test kit 1 may be housed in the case 50 as is. Furthermore, stoppers may be provided in the cover 51 and the case 52 for locking the cover 51.

<Behavior Within Test Kit>

The following provides a brief explanation of behavior within the test kit 1 resulting from the dropping of a liquid sample.

As has been described above, the absorbency of the immobilizing membrane 15 of the kit body 10 is set to be higher than the absorbency of any region of the multifunctional member 17. In addition, in the multifunctional member 17, the absorbency of the backflow prevention region 173 is set to be higher than the absorbencies of the labeling substance holding region 172 and the sample dropping region 171. As a result of arranging these in the manner described above, a liquid sample dropped onto the sample dropping region 171 of the test kit 1 flows in the manner indicated below.

The liquid sample develops though the liquid dropping region 171 and is absorbed by the backflow prevention region 173 through the interface b1 at an absorbency higher than when developing through the sample dropping region 171.

Liquid sample that has flown into the backflow prevention region 173 develops vigorously (at high absorbency) and slowly downstream.

The liquid sample is then absorbed by the labeling substance holding region 172 through the interface b2 at a weaker force (lower absorbency) than when developing through the backflow prevention region 173.

At this time, the liquid sample flows from the interface b2 only into the non-containing portion 172a. The liquid sample then causes the labeling substance held in the containing portion 172b to flow out while gently flowing towards the containing portion 172b from the non-containing portion 172a.

The labeling substance that has flown out is absorbed through the interface d1 by the immobilizing membrane 15 together with the liquid sample at a stronger force (higher absorbency) than when developing through the labeling substance holding region 172.

At this time, liquid sample remaining in the non-containing portion 172a causes the labeling substance to flow out even after the majority of the labeling substance has flown out from the containing portion 172b.

In the case a substance to be detected is contained in the liquid sample, a labeled complex is formed during development in which the labeled substance has specifically bound to the substance to be detected. The labeled complex then binds to the immobilized sample in the detection zone 15a and is labeled in the form of a test line.

Liquid sample that has developed through the immobilizing membrane 15 is absorbed by the absorbent pad 20 after having reached the interface d2.

On the basis of the above, as a result of providing the non-containing portion 172a upstream of the containing portion 172b in the labeling substance holding region 172, liquid sample flows into the containing portion 172b from the non-containing portion 172a having a uniform fiber opening size, thereby making it possible to inhibit disturbances in the liquid sample in the containing portion 172b and inhibit retention of labeling substance caught therein.

Furthermore, the size of fiber openings of the labeling substance holding region 172 is not required to be uniform provided a configuration is employed that is capable of inhibiting disturbances in the liquid sample that flows into the containing portion 172a.

Furthermore, as a result of providing the backflow prevention region 173 having higher absorbency than the non-containing portion 172a upstream of the non-containing portion 172a, disturbances in the flow of the liquid sample that flows into the non-containing portion 172a can be inhibited, thereby making it possible to inhibit retention of the labeling substance. In addition, in the test kit 1, as a result of connecting an end surface of the non-containing portion 172a and an end surface of the backflow prevention region 173 in mutual adjacency, in comparison with the case of arranging the region on the upstream side superimposed on the non-containing portion 172a, in addition to being able to decrease the area of the interface b2, liquid sample is able to flow in without being affected by gravity. As a result, disturbances in the flow of the liquid sample can be suppressed and retention of the labeling substance can be further inhibited.

In addition, even if the labeling substance has flown into the non-containing portion 172a from the containing portion 172b, since the backflow prevention region 173 is present between the non-containing portion 172a and the liquid dropping region 171, backflow of the liquid sample containing the labeling substance into the sample dropping region 171 can be prevented.

According to the above-mentioned configuration, a liquid sample can be made to flow out more rapidly to the immobilizing membrane 15, and remaining liquid sample is able to further promote the flow of the labeling substance, thereby making it possible to carry out rapid and highly sensitive detection.

In addition, assembly of the multifunctional member 17 of the test kit 1 can be facilitated since it is integrally formed.

Although the multifunctional member 17 was integrally formed with a single member in the above-mentioned first embodiment, it is not limited thereto. For example, the multifunctional member 17 may be in the form of a single member obtained by using different types of members (such as fibrous members having different opening sizes) for each region and joining these members. In addition, a plurality of members, for example, may be arranged connected on the kit body 10 instead of using a single member. In this case, the arrangement of the members composing each region of the multifunctional member 17 is not limited to that shown in FIG. 3.

For example, as shown in FIG. 6, a multifunctional member 17A may have a backflow prevention region 173A arranged below a sample dropping region 171A, and a labeling substance holding region 172A may be arranged below the backflow prevention region 173A. At this time, preferably only the upper surface of a non-containing portion 172Aa of the labeling substance holding region 172A contacts the lower surface of the backflow prevention region 173A. Furthermore, the range over which the lower surface of the backflow prevention region 173A makes contact may be of any degree provided it contacts the upper surface of the non-containing portion 172Aa.

In addition, as shown in FIG. 7, for example, in a multifunctional member 17B, a backflow prevention region 173B may be arranged downstream of a sample dropping region 171B so as to be adjacent thereto, and a labeling substance holding region 172B may be arranged below the backflow prevention region 173B.

Second Embodiment

The following provides an explanation of a test kit according to a second embodiment with reference to the drawings. FIG. 8 is a lateral cross-sectional view showing a state in which the test kit according to the second embodiment has been housed in a case.

In a test kit 1A according to the present embodiment, a fibrous material having a uniform opening size (namely, uniform absorbency) is used instead of the multifunctional member 17. When using the test kit 1A, a backflow prevention region is formed by pressing an intermediate portion of the sheet member 27 in the lengthwise direction at a desired pressure. More specifically, for example, the sheet member 27 is pressed at a desired pressure when housed in a case 60. The following provides an explanation thereof.

The sheet member 27 has a containing region 27B that uniformly contains a labeling substance. The containing region 27B is formed by impregnating one end portion of the sheet member 27 in the lengthwise direction with a solution containing the labeling substance, followed by drying. Furthermore, the labeling substance is not held in a region 27A constituting a region other than the containing region 27B of the sheet member 27.

The case 60 has a case body 62 that houses the test kit 1 and a cover 61 that covers the case body 62. For example, a plurality of projecting portions 621 for positioning the test kit 1 are provided rising from the case body 62. An opening 611 for dropping a liquid sample onto the sample dropping region 171 and an opening 612 for viewing a test line on the immobilizing membrane 15 are formed in the cover 61. A pressing portion 613 for forming a backflow prevention region in the sheet member 27 is formed in the cover 61. In the case the test kit 1 is housed in the case body 62, fibers of an intermediate region of the sheet member 27 in the lengthwise direction are crushed by the pressing portion 613, resulting in higher absorbency than other regions located upstream and downstream of the sheet member 27. As a result, together with the backflow prevention region being formed in an intermediate region of the sheet member 27, a sample dropping region and labeling substance holding region that have lower absorbencies than the backflow prevention region are formed on the upstream side and downstream side of the backflow prevention region, respectively.

In the above-mentioned embodiment, as a result of providing the pressing portion 613 in the case 60, production can be simplified without having to process the sheet member 27 prior to incorporating in the case 60. Furthermore, a projection 614 may also be provided in the cover 61 for pressing the downstream side of the immobilizing membrane 15 (for example, in the vicinity of the interface d2 between the absorbent pad 20 and the immobilizing membrane 15 farther downstream than the location of the test line). As a result, fibers on the downstream side of the immobilizing membrane 15 are crushed and the liquid sample is able to flow smoothly.

Although only the pressing portion 613 for forming a backflow prevention region in an intermediate region of the sheet member 27 is formed in the cover 61 of the case 60 in the above-mentioned embodiment, it is not limited thereto. For example, a pressing portion for forming a labeling substance holding region may also be formed in the cover 61 in addition to the pressing portion 613 (although not shown, this pressing portion is generically explained in the subsequent description as a second pressing portion). More specifically, the second pressing portion is arranged adjacent to the downstream side of the pressing portion 613, and is formed so as to press a prescribed range of the end portion on the downstream side of the sheet member 27 that includes the containing portion 27B. In addition, the second pressing portion is formed thinner than the pressing portion 613 in the vertical direction. As a result, a region that has been pressed by the pressing portion 613 is subjected to greater pressure than the region pressed by the second pressing member, resulting in greater crushing of the fiber openings and increased absorbency. In addition, since the fiber openings of those regions not contacted by either pressing portion are not crushed, absorbency is set lower than those portions where the fiber openings are crushed.

According to the above-mentioned configuration, in the case the test kit 1 has been housed in the case body 62, a liquid dropping region where pressure is not applied is formed on the upstream side of the sheet member 27, a labeling substance holding region pressed by the second pressing portion is formed on the downstream side of the sheet member 27, and a backflow prevention region pressed at a higher pressure (by the pressing portion 613) than that of the second pressing portion is formed between the sample dropping region and the labeling substance holding region. As a result, since the difference in absorbency between the backflow prevention region and the labeling substance holding region is gradual, the liquid sample is able to flow smoothly from the backflow prevention region to the labeling substance holding region.

In addition, although the pressing portion 613 (and similarly, the second pressing portion) was formed in the cover 61 of the case 60 in the above-mentioned embodiment, it is not limited thereto. For example, these pressing portions may also be formed protruding from the bottom of the case body 62. Moreover, restraining members and the like may be used that use a prescribed pressing force to restrain an intermediate region of the sheet member 27 from above and below instead of using the case 60.

Although the preceding description has provided an explanation of several embodiments of the present invention, these embodiments are provided as examples for explaining the present invention, and it is not intended to limit the scope of the present invention to only the embodiments described above. The present invention can also be carried out in various other forms.

REFERENCE SIGNS LIST

1 Test kit
10 Kit body
17 Multifunctional member
15 Immobilizing membrane
20 Absorbent pad
30 Sheet
171 Sample dropping region
172 Labeling substance holding region
172*a* Non-containing portion
172*b* Containing portion
173 Backflow prevention region

The invention claimed is:

1. A test kit for detecting a substance to be detected a liquid sample, the test kit comprising:
   a first member, the first member comprising a dropping region located furthermost upstream onto which the liquid sample is dropped, a labeling substance holding region comprising a containing portion and a non-containing portion, and a backflow prevention region, wherein:
      the containing portion contains a labeling substance consisting of a label and a binding substance that binds the substance to be detected wherein the label is immobilized on the binding substance;
      the non-containing portion is located upstream of the containing portion and does not contain the labeling substance;
      the backflow prevention region is composed of a fibrous member material having finer opening size than the fibrous member material at the dropping region and the labeling substance region, the backflow prevention region further comprising a compressed region of the first member; and
      the backflow prevention region is located between the dropping region and the non-containing portion of the labeling substance holding region, the backflow prevention region separated from the containing portion by the non-containing portion; and
   a second member comprising a detection zone for capturing the labeling substance, wherein:
      the labeling substance is captured through the substance to be detected; and
      the second member is downstream of the first member in the developing direction and the upstream end of the second member is in contact with the labeling substance holding region of the first member, thereby allowing the labeling substance to flow with the liquid sample from the first member to develop at the detection zone at the second member.

2. The test kit of claim 1, further comprising a case that houses the first and second members, wherein the compressed region of the backflow prevention region is formed by the pressing portion.

3. The test kit of claim 1, wherein the containing portion of the labeling substance holding region is formed by impregnating the first member with a solution containing the labeling substance followed by drying.

4. The test kit of claim 1, wherein the non-containing portion is separated from the second member by the containing portion.

* * * * *